US009763399B2

(12) United States Patent
De Groot et al.

(10) Patent No.: US 9,763,399 B2
(45) Date of Patent: Sep. 19, 2017

(54) DUAL PURPOSE POLLENIZER WATERMELONS

(71) Applicant: Nunhems B.V., Nunhem (NL)

(72) Inventors: Erik De Groot, Nonantola (IT); Elena Chiapparino, Bologna (IT)

(73) Assignee: NUNHEMS B.V., Nunhem (NL)

( * ) Notice: Subject to any disclaimer, the term of this patent is extended or adjusted under 35 U.S.C. 154(b) by 941 days.

(21) Appl. No.: 13/933,842

(22) Filed: Jul. 2, 2013

(65) Prior Publication Data

US 2014/0020139 A1 Jan. 16, 2014

Related U.S. Application Data

(63) Continuation-in-part of application No. 13/849,269, filed on Mar. 22, 2013, now abandoned, which is a continuation-in-part of application No. 13/681,388, filed on Nov. 19, 2012, which is a continuation-in-part of application No. 13/518,789, filed as application No. PCT/EP2011/070817 on Nov. 23, 2011, now abandoned.

(60) Provisional application No. 61/416,908, filed on Nov. 24, 2010.

(51) Int. Cl.
| | |
|---|---|
| *A01H 5/08* | (2006.01) |
| *A01H 1/02* | (2006.01) |
| *C12N 5/04* | (2006.01) |
| *A01H 4/00* | (2006.01) |
| *A01H 5/00* | (2006.01) |
| *A23L 19/00* | (2016.01) |

(52) U.S. Cl.
CPC ............... *A01H 5/08* (2013.01); *A01H 5/00* (2013.01); *A23L 19/00* (2016.08)

(58) Field of Classification Search
CPC .................................................... A01H 5/08
See application file for complete search history.

(56) References Cited

U.S. PATENT DOCUMENTS

| | | | |
|---|---|---|---|
| 7,314,979 | B2 | 1/2008 | Lanini et al. |
| 7,550,652 | B2 | 6/2009 | Zhang |
| 7,820,884 | B2 | 10/2010 | Zuckerbraun |
| 2006/0005284 | A1 | 1/2006 | Tolla et al. |
| 2006/0168701 | A1 | 7/2006 | Zhang et al. |
| 2009/0288183 | A1 | 11/2009 | Zuckerbraun |
| 2013/0152223 | A1* | 6/2013 | De Groot ............... A01H 5/00 800/308 |
| 2013/0232636 | A1 | 9/2013 | De Groot et al. |
| 2014/0020127 | A1 | 1/2014 | De Groot et al. |

FOREIGN PATENT DOCUMENTS

| | | |
|---|---|---|
| WO | 00/70933 | 11/2000 |
| WO | WO 00/70933 | 11/2000 |
| WO | WO 03/051103 | 6/2003 |
| WO | 03075641 | 9/2003 |
| WO | WO 03/075641 | 9/2003 |

OTHER PUBLICATIONS

Dittmar. "NCSU Libraries Online Catalog: Characterization of diploid watermelon pollenizers and utilization for optimal triploid watermelon production and effects of halosulfuron post and post-directed on watermelon [electronic resource]." Catalog.lib.ncsu.edu. n.d. Web. Aug. 4, 2016. <http://catalog.lib.ncsu.edu/record/NCSU1960390> Published: 2006.*
GRIN PI-368510, first available in 1972.*
P.J. Dittmar, Characterization of diploid watermelon pollenizers and utilization for optimal triploid watermelon production and effects of halosulfuron post and post-dir on watermelon, Thesis Graduate Faculty of North Carolina State University, Horticultural Science 2006.
X. Zhang, K. Ma, M. Wang, Nutrients in Seeds of Edible Watermelon (Citrullus lanatus (Thunb.) Matsum, and Nakai, Report 1990 (13), pp. 43-44.
N. Guner and T.C. Wehner, The Genes of Watermelon, HortScience 2004 39(6), pp. 1175-1182.
K.L. Bett, Chapter 13. Evaluating Sensory Quality of Fresh-cut Fruits and Vegetables, Fresh-cut fruits and vegetables, CRC Press 2002, pp. 427-438.
W.S. Barham, A Study of the Royal Golden Watermelon with Emphasis on the Inheritance of the Chlorotic Condition Characteristic of This Variety, Proccedings of the American Society for Horticultural Science 1965 (67), pp. 487-489.
H. Kihara, Triploid Watermelons, Proceedings of the American Society for Horticultural Science 1951 (58), pp. 217-230.
Haikun et al, Evaluation on Crack Resistance of Watermelon (Citrullus lanatus), Acta Horticulturae 2010 (871), pp. 223-230.
O.J. Eigsti, About Our Cover, HortScience 1971 (6(1)), pp. 1-2.
J. Zhang, Breeding and Production of Watermelon for Edible Seed in China, Report 1996 (19), pp. 66-67.
Barham, A Study of the Royal Golden Watermelon with Emphasis on the Inheritance of the Chlorotic Condition Characteristic of This Variety, *Proceedings of the American Society for Horticultural Science* 1965 (67), pp. 487-489.
Bett, Chapter 13. Evaluating Sensory Quality of Fresh-cut Fruits and Vegetables, Fresh-cut Fruits and Vegetables, *CRC Press* 2002, pp. 427-438.
Dittmar, Characterization of diploid watermelon pollenizers and utilization for optimal triploid watermelon production and effects of halosulfuron post and post-dir on watermelon, Thesis Graduate Faculty of North Carolina State University, *Horticultural Science* 2006.
Dittmar, Maximum Potential Vegetative and Floral Production and Fruit Characteristics of Watermelon Pollenizers, *HortScience* 2009 44(1), pp. 59-63.

(Continued)

*Primary Examiner* — Lee A Visone
(74) *Attorney, Agent, or Firm* — Arent Fox LLP

(57) ABSTRACT

The application relates to the field of plant breeding, in particular watermelon breeding. Provided are diploid watermelon plants (and seeds from which these plants can be grown) which produce small, diploid, red watermelon fruits. Also provided are small, diploid watermelon fruits having an average weight of less than 1.8 kg.

13 Claims, 2 Drawing Sheets

(56) References Cited

OTHER PUBLICATIONS

Eigsti, About Our Cover, *HortScience* 1971 (6(1)), pp. 1-2.
Guner & Wehner, The Genes of Watermelon, *HortScience* 2004 39(6), pp. 1175-1182.
Kihara, Triploid Watermelons, *Proceedings of the American Society for Horticultural Science* 1951 (58), pp. 217-230.
Haikun, et al., Evaluation on Crack Resistance of Watermelon (Citrullus lanatus), *Acta Horticulturae* 2010 (871 ), pp. 223-230.
Zhang, Breeding and Production of Watermelon for Edible Seed in China, *Report* 1996 (19), pp. 66-67.
Zhang, et al., Nutrients in Seeds of Edible Watermelon ( *Citrullus lanatus* (Thunb.) Matsum, and Nakai, *Report* 1990 (13): 43-44.
International Search Report for PCT/EP2011/070817 dated Dec. 30, 2011.
Haikun, et al., Evaluation on Crack Resistance of Watermelon (Citrullus lanatus), *Acta Horticulturae* 2010 (871), pp. 223-230.
Zhang, et al., Nutrients in Seeds of Edible Watermelon (*Citrullus lanatus* (Thunb.) Matsum, and Nakai, *Report* 1990 (13): 43-44.

\* cited by examiner

DUAL PURPOSE POLLENIZER WATERMELONS

CROSS-REFERENCE TO RELATED APPLICATIONS

This application is a continuation-in-part of U.S. patent application Ser. No. 13/849,269, filed Mar. 22, 2013, which is a continuation-in-part of U.S. patent application Ser. No. 13/681,388, filed Nov. 19, 2012, which is a continuation-in-part of U.S. patent application Ser. No. 13/518,789, filed Jun. 22, 2012, which is the U.S. national stage application of PCT/EP2011/070817, filed Nov. 23, 2011, which claims the benefit of U.S. Provisional Patent Application 61/416,908, filed Nov. 24, 2010, the contents of each of which are hereby incorporated by reference in their entirety.

FIELD OF THE INVENTION

The present invention relates to the field of watermelon breeding and watermelon improvement. Provided are new diploid watermelon plants ($2n=2x=22$) and seeds from which such plants can be grown, which produce very small diploid fruits. The diploid watermelon plants are preferably suitable as pollenizers in triploid watermelon ($2n=3x=33$) production, whereby the pollenizers therefore have a dual purpose: providing sufficient viable pollen to pollinate female flowers of triploid plants (which after pollination produce triploid, seedless watermelon fruits) and/or to provide small ("mini"- or personal size), edible diploid fruits on the pollinizer plants themselves. The fruits are so small, that they can be easily treated like apples, i.e. they can be eaten fresh after e.g. removing the rind, or they can be eaten with a spoon after cutting in half or removing a slice from fruit. Alternatively, the whole fruit can be eaten, i.e. including the rind.

BACKGROUND OF THE INVENTION

Seedless watermelon (*Citrullus lanatus* (Thunb.) Matsum. And Nak.) production involves using pollen from diploid male parent plants to fertilize flowers of tetraploid ($2n=4x=44$) maternal parent plants. Pollination of the tetraploid flowers with diploid pollen leads to hybrid F1 seeds which are triploid (Kihara, 1951, Proceedings of American Society for Horticultural Science 58: 217-230; Eigsti 1971, Hort Science 6: 1-2). The triploid hybrid plants, grown from these F1 seeds, are self-infertile as they produce sterile pollen due to chromosome imbalance (Fehr, 1987). The triploid hybrids, therefore, need to be pollinated by a diploid pollenizer to produce watermelon fruit. Triploid plants are, therefore, interplanted with pollenizer plants for fruit production. The "seedless" fruit produced after pollination on the triploid hybrid plant are often not truly seedless, but may contain some undeveloped, small, pale seeds, which are edible.

For optimal seedless watermelon fruit set, sufficient viable pollen is required. Plants are generally planted at a ratio of 1 pollenizer per every 2-4 triploid plants. Triploid plants and pollenizers are either planted in separate rows (e.g. 1 row of pollenizer and 2-4 rows of triploids), or interplanted within rows (e.g. planting 1 pollenizer plant in between 2 to 3 triploid plants in the same row), or interplanted in narrow rows between rows of triploids (see US 2006/0168701 Table 2). The fruit produced on the pollenizer plants preferably has a different rind pattern from the fruit on the triploid hybrids, so that these can be easily distinguished. Until now, generally the fruits produced on dedicated pollenizer plants are not harvested or discarded and only the seedless triploid fruits are sold.

In the last years, several dedicated pollenizer plants have been developed, which provide sufficient staminate flowers and sufficient viable pollen throughout the season to increase triploid fruit yield. These dedicated pollenizers include for example varieties Polimax and Jenny (Nunhems), Sidekick (Harris Morin), Companion (Seminis) and the Super-Pollenizers SP-1 and SP-4 (Syngenta). These dedicated pollenizers can be divided into two categories based on their vegetative growth type, which is either of the standard vine length e.g. Jenny and SP-1 and SP-4, or the 'compact' vine length, e.g. Companion or Sidekick.

Some pollenizers produce diploid fruits which could be marketable, while others produce fruits that are unsuitable for consumption and marketing. Dittmar (2006, MSc Thesis North Carolina State University, Horticultural Science, Characterization of diploid watermelon pollenizers and utilization for optimal triploid watermelon production and effects of halosulfuron post and post-dir on watermelon) evaluated different pollenizers for the potential marketability of their fruits and concluded that Mickeylee, SF800, MiniPool, Jenny and Pinnacle have a fruit quality that could potentially be marketed. Average fruit weight of these was 5.1 kg, 10.7 kg, 3.9 kg, 3.3 kg and 2.9 kg respectively (Dittmar 2006, supra). The smallest diploid fruits were produced by Sidekick (1.0 kg, with dimensions of 12.3×11.9 cm length:width Dittmar 2006, supra) and SP-1 (2.0 kg, with dimensions of 17.5×15.4 cm length:width (Dittmar 2006, supra), but neither of these produce marketable fruits. The fruits of Sidekick are very poor quality pink-fleshed and those of SP-1 are white-fleshed and have a low brix value. Due to the non-marketable fruits, these pollenizers are referred to as being "non-harvestable pollenizers".

US2009/0288183 (Gold Seed Co. LLC) describe a pollinizer called "Escort-4" which produces small fruits having reduced sugar for type 2 diabetics, referred to as a "dual purpose reduced sugar watermelon". The fruits are said to have an average weight of 4.0 lbs (1.8 kg) and a size of 5-7 inches long (12.7-17.7 cm)×4-5 inches wide (10.1-12.7 cm). The fruits of Escort-4 are said to have approximately ⅓ less sugar content than commercial diploid varieties, such as Sangria (Syngenta Inc.).

SUMMARY OF VARIOUS EMBODIMENTS OF THE INVENTION

It is an object of the invention to provide dual purpose watermelon pollenizers producing small, edible (i.e. marketable) diploid fruit with an average fruit weight of less than 2.0 kg, preferably less than 1.8 kg or 1.7 kg, more preferably equal to or less than 1.6, 1.5, 1.4, 1.3, 1.0, 0.9, 0.8, 0.7 kg, and even more preferably equal to or less than about 0.65 kg, such as equal to or less than 0.6 kg, 0.5 kg, 0.4 kg or 0.3 kg. In one embodiment the fruits are preferably red fleshed, more preferably dark red fleshed, with e.g. a RHS rating of 39 or higher (not pink red or coral red or yellow-red). In another embodiment the average fruit brix is at least about 7.5% or higher.

It is a further object of the invention to provide dual purpose watermelon pollenizers producing small, edible (i.e. marketable) diploid fruit with an average fruit weight of less than 0.9 kg, such as equal to or less than 0.8 kg, 0.7 kg, 0.65 kg, 0.6 kg, 0.5 kg, 0.4 kg or 0.3 kg, but above 0.25 kg. In one embodiment the fruits are preferably red fleshed, more preferably dark red fleshed with e.g. a RHS rating of 39 or higher (not pink red or coral red or yellow-red). In another embodiment the average fruit brix is at least about 7.5% or higher.

The invention also provides for the following, in addition to all aspects provided in the general description below:

Aspect 1. A plant of the species *Citrullus lanatus* wherein said plant is diploid and produces edible (and marketable), diploid fruits and which is designated WH9716; or a plant of the species *Citrullus lanatus* wherein said plant is diploid and produces edible (and marketable), diploid fruits and which is designated WH9717, or a part of said plant; or a plant of the species *Citrullus lanatus* wherein said plant is diploid and produces edible (and marketable), diploid fruits and which is designated WH9721, or a part of said plant; a representative sample of seeds of WH9716, having been deposited under Accession Number NCIMB 42704.

Aspect 2. A plant, which does not (statistically) significantly differ from any of the plant of aspect 1 in the following characteristics when grown under the same conditions: 1) Mature fruit length, 2) mature fruit diameter, and 3) mature fruit weight.

Aspect 3. A plant which does not significantly differ from any of the plant of aspect 1 in the following characteristics when grown under the same conditions: 1) Mature fruit length, 2) mature fruit diameter, and 3) mature fruit weight, and which further does not significantly differ from the plant of anyone of aspect 1 in one or more or all of the following characteristics when grown under the same conditions: 4) Number of male flowers, 5) Compact vine type (i.e. ratio vine length/number of internodes, see Table 9) the average stem diameter at the second node, 7) the rind thickness at blossom end, 8) the rind thickness at the sides, 9) the % placental separation, 10) the % traverse crack, 11) the number of seeds per fruit.

Aspect 4. A seed designated WH9716, a representative sample of seeds having been deposited under Accession Number NCIMB 42704; or a seed designated WH9717; or a seed designated WH9721.

Aspect 5. A plant, or a part thereof, produced by growing the seed of aspect 4.

Aspect 6. The plant or part thereof of aspect 1 or 2, produced by in vitro culture or by grafting of a scion derived from WH9716, or WH9717, or WH9721 to a different rootstock; a representative sample of seeds of WH9716 having been deposited under Accession Number NCIMB 42704.

Aspect 7. A (edible and marketable) fruit produced on the plant of anyone of aspect for 2 or aspect 5. In a preferred aspect, the whole fruit is edible, i.e. including the rind; thus, the rind is preferably between about 0.2 cm and 0.5 cm thick on the sides, more preferably at least about 0.2 cm, 0.3 cm or 0.4 cm, but less than 0.5 cm. In one aspect the rind thickness on the side is 0.2 to 0.3 cm.

Aspect 8. A plant cell culture or tissue culture of the plant or part thereof of aspect 1 or 2 or of the seed or part of the seed of aspect 4.

Aspect 9. The plant part of aspect 1 or 2 or 5, wherein the part is selected from the group consisting of: a scion, a rootstock, a cell, a cutting, a cotyledon, a fruit, a shoot, a shoot tip, a seed, a root, a hypocotyl, an embryo, a protoplast, a leaf, a meristem, a flower or a stem, or a part of any of these.

Aspect 10. A watermelon plant which is regenerated from the plant part of aspect 1 or 2 or 5, wherein the part is selected from the group consisting of: a scion, a rootstock, a cell, a cotyledon, a fruit, a shoot, a shoot tip, a hypocotyl, an embryo, a seed, a protoplast, a leaf, a meristem, a flower or a stem, or a part of any of these, and wherein the regenerated plant does not significantly differ from the plant of anyone of aspects 1 in the following characteristics when grown under the same conditions: 1) Mature fruit length, 2) mature fruit diameter, and 3) mature fruit weight.

Aspect 11. The watermelon plant which is regenerated from the plant part of anyone of aspect 1 or 2 or 5, wherein the part is selected from the group consisting of: a scion, a rootstock, a cell, a cotyledon, a fruit, a shoot, a shoot tip, a hypocotyl, an embryo, a seed, a protoplast, a leaf, a meristem, a flower or a stem, cutting or a part of any of these, and wherein the regenerated plant does not significantly differ from the plant of anyone of aspect 1 in the following characteristics when grown under the same conditions: 1) Mature fruit length, 2) mature fruit diameter, and 3) mature fruit weight, and which further does not significantly differ from the plant of aspect 1 in one or more of the following characteristics when grown under the same conditions: 4) Number of male flowers, 5) Compact vine type (i.e. ratio vine length/number of internodes, 6) the average stem diameter at second node, 7) the rind thickness at blossom end, 8) the rind thickness at sides, 9) the placental separation, 10) the % traverse crack, 11) the number of seeds per fruit.

Aspect 12. A plant which is regenerated from the part of aspect 9 and which has essentially all the morphological and/or physiological characteristics of WH9716, WH9717, or WH9721, respectively when grown under the same conditions, a representative sample of seeds of WH9716 having been deposited under Accession Number NCIMB 42704.

Aspect 13. A watermelon plant which is regenerated from the part of aspect 9 and which has essentially all the morphological and/or physiological characteristics of WH9716, WH9717, or WH9721 when grown under the same conditions, except that it is significantly different from WH9716, WH9717, or WH9721 in 1, 2, 3, 4 or 5 characteristics, a representative sample of seeds of WH9716, WH9717, WH9721 having been deposited under Accession Number NCIMB 42704.

Aspect 14. A (edible and marketable) fruit produced on the plant of aspect 10, 11, 12 or 13. In a preferred aspect, the whole fruit is edible, i.e. including the rind; thus, the rind is preferably between about 0.2 cm and 0.5 cm thick on the sides, more preferably at least about 0.2 cm, 0.3 cm or 0.4 cm, but less than 0.5 cm. In one aspect the rind thickness on the side is 0.2 to 0.3 cm.

Aspect 15. A watermelon plant derived the watermelon plant or plant part of anyone of aspect 1 or aspect 2 or aspect 5, having at least one, two or three physiological and/or morphological characteristics which are different from those of WH9716, WH9717, WH9721, respectively and which otherwise has essentially all physiological and morphological characteristics of a watermelon plant designated WH9716, WH9717, WH9721, respectively when grown under the same conditions, a representative sample of seeds of WH9716 having been deposited under Accession Number NCIMB 42704.

Aspect 16. The plant of aspect 15, obtained by selecting a natural or induced mutant, or a somaclonal variant from a population of plants or from plant parts or from seeds of WH9716, WH9717, or WH9721; a representative sample of seeds of WH9716 having been deposited under Accession Number NCIMB 42704.

Aspect 17. A method for producing diploid and triploid watermelon fruits in one field, said method comprising:

a) interplanting a triploid watermelon plant and a diploid plant of anyone of aspect 1, or 2, or or 11, or 12, or 13, or 15, in one field:

b) allowing the pollen of the diploid plant to pollinate the flowers of the triploid plant and of the flowers of the plant of anyone of aspect 1, or 2, or 10, or 11 or 12 or 13 or 15, respectively, c) harvesting fruits produced on the triploid hybrid plants and optionally the fruit from the plants of anyone of aspect 1, or 2, or 10, or 11 or 12 or 13 or 15, respectively; and optionally d) packaging the fruits into containers.

Aspect 18. The seed of anyone of aspect 4, wherein the seed is primed and/or wherein the seed further comprises one or more compounds or compositions selected from: a biological control agent, a fungicidal composition, a insecticidal composition, a nematicidal composition or an acaricidal composition.

Aspect 19. The plant of anyone of aspect 1 or 2, wherein the plant comprises a different rootstock.

Aspect 20. The plant of aspect 1 or 2 or 10 or 11 or 12 or 13, wherein the plant comprises a different rootstock.

Aspect 21. The plant of aspect 15, wherein the plant comprises a different rootstock.

In one embodiment the invention relates to a plant comprising a first set of chromosomes of any of the plants WH9716, or WH9717, or WH9721, a representative sample of seeds of WH9716 having been deposited under Accession Number NCIMB 42701.

In yet another embodiment the invention relates to a seed comprising a first set of chromosomes of any of the plants WH9716, or WH9717, or WH9721, a representative sample of seeds of WH9716 having been deposited under Accession Number NCIMB 42701.

General Definitions

The verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one", e.g. "a plant" refers also to several cells plants, etc. Similarly, "a fruit" or "a plant" also refers to a plurality of fruits and plants.

As used herein, the term "plant" includes the whole plant or any parts or derivatives thereof, preferably having the same genetic makeup as the plant from which it is obtained, such as plant organs (e.g. harvested or non-harvested fruits, leaves, etc.), plant cells, plant protoplasts, plant cell- or tissue-cultures from which whole plants can be regenerated, plant calli, plant cell clumps, plant transplants, seeds from which the plant can be grown and seeds produced by the plant, seedlings, plant cells that are intact in plants, plant clones or micropropagations, or parts of plants, such as plant cuttings, embryos, pollen, ovules, fruits (e.g. harvested tissues or organs), flowers, leaves, clonally propagated plants, roots, stems, root tips, grafts (scions and/or root stocks) and the like. Also any developmental stage is included, such as seedlings, cuttings prior or after rooting, etc.

It is, thus, understood that herein a watermelon plant, such as a triploid plant or pollenizer plant, encompasses not only an ungrafted plant, but also a plant with a rootstock of a different plant, such as a gourd or squash rootstock, another watermelon rootstock, a transgenic rootstock, etc.

As used herein, the term "variety" or "cultivar" means a plant grouping within a single botanical taxon of the lowest known rank, which can be defined by the expression of the characteristics resulting from a given genotype or combination of genotypes.

The term "allele(s)" means any of one or more alternative forms of a gene at a particular locus, all of which alleles relate to one trait or characteristic at a specific locus. In a diploid cell of an organism, alleles of a given gene are located at a specific location, or locus (loci plural) on a chromosome. One allele is present on each chromosome of the pair of homologous chromosomes. A diploid plant species may comprise a large number of different alleles at a particular locus. These may be identical alleles of the gene (homozygous) or two different alleles (heterozygous).

The term "locus" (loci plural) means a specific place or places or a site on a chromosome where for example a gene or genetic marker is found.

"Diploid plant" refers to a plant, vegetative plant part(s), or seed from which a diploid plant can be grown, having two sets of chromosome, designated herein as 2n.

"Triploid plant" refers to a plant, vegetative plant part(s), or seed from which a triploid plant can be grown, having three sets of chromosomes, designated herein as 3n.

"Tetraploid plant" refers to a plant, vegetative plant part(s), or seed from which a tetraploid plant can be grown, having four sets of chromosomes, designated herein as 4n.

"Pollenizer plant" or "pollenizer" refers to the (inbred or hybrid) diploid plant, or parts thereof (e.g. its pollen or scion), suitable as pollenizer for inducing fruit set on triploid plants. A pollenizer plant is, thus, able to lead to good fruit set (and good triploid fruit yield) of triploid plants, by producing an appropriate amount of pollen at the appropriate day-time and for an appropriate period of time, e.g. at least during peak flowering time of the triploid female plants. A good triploid fruit yield is, for example, a yield comparable to the yield obtainable when using Polimax (produced by Nunhems) as pollenizer (see e.g. Example 3).

"Dual purpose pollenizer" refers to a pollenizer plant which also produces edible diploid fruits on the pollenizer plant itself (through self-pollination) and also is suitable to be used as a pollenizer in triploid (seedless) watermelon production. This definition is independent of whether or not the plant is actually being used as a pollenizer in triploid fruit production, i.e. it can also be used for diploid fruit production on its own.

The term "edible" is used herein to refer to fruits marketable for human consumption, especially fresh consumption of the fruit flesh. The fruits have at harvest at least good, preferably very good flavor properties (i.e. taste and odor). To have good flavor properties the fruits preferably have an average level of Total Soluble Solids of at least about 7.5% or more. Good fruit flesh color is also an important criterion for marketability for human consumption. For red-fleshed fruits it is an embodiment that the flesh color has an average RHS rating of at least 39 or above. If red-fleshed fruits are measured on a scale of 1 (white) to 10 (dark red), the fruits have an average rating of at least 7 or more. If red-fleshed fruits are measured on a USDA scale of 1 to 6 (1=white, 2=yellow, 3=orange, 4=pink, 5=red and 6=dark red), red fruits have a rating of 5 or 6.

"Hybrid triploid plant" is a triploid plant grown from hybrid, triploid seed obtained from cross fertilizing a male diploid parent with a female tetraploid parent.

"Seedless fruit" are triploid fruit which contain no or few mature seeds. The fruit may contain one or more small, edible, white ovules. Plants which produce seedless fruit may herein be referred to as "seedless".

"Interplanting" refers to the combination of two or more types of seeds and/or transplants sown or transplanted on the same field, especially the sowing and/or transplanting of pollenizers in the same field as triploid hybrid plants (for seedless fruit production on the triploid plants and diploid fruit production on the pollenizer plants). For example, the pollenizer may either be planted in separate rows or interplanted with the triploid plants in the same row (e.g. in hills within each row). Pollenizers may also be planted in between rows of triploids. Also seeds of pollenizers and triploid hybrids may be mixed prior to seeding, resulting in random seeding. The transplants of the triploid hybrid plants and/or pollenizer plants may also comprise a rootstock of a different plant. Suitable rootstocks are known in the art. Also encompassed are methods where the triploid hybrid plant and the pollenizer plant are grafted together onto one rootstock.

"Planting" or "planted" refers to seeding (direct sowing) or transplanting seedlings (plantlets) into a field by machine or hand.

"Vegetative propagation" refers to propagation of plants from vegetative tissue, e.g. by in vitro propagation or grafting methods (using scions).

"Vegetative type" or "growth type" or "vine type" refers to the combination of growth characteristics of the vegetative parts of a plant line or variety, such as (average) internode length, (average) length of the main vine, (average) length of the shortest and longest branch, average number of primary branches, etc. Three vegetative types can be distinguished: The "normal/standard vine type", the "compact vine type" and an "intermediate vine type" between these two.

"Compact vine type" refers to the vegetative type of a plant or plant line or variety having an average internode length of about 4.0-6.5 cm, especially an average internode length of equal to or below 6.5 or 6.0 cm, e.g. equal to or below 5.0, 4.5 or 4.0 cm and/or an average longest branch of equal to or less than about 170 cm, preferably 160 cm, preferably equal to or less than 150 cm or 145 cm, preferably equal to or less than 140 or 130 cm. Examples of compact vine types are Companion and Sidekick (U.S. Pat. No. 7,314,79).

A "standard vine type" refers to the vegetative type of a plant or plant line or variety having an average internode length of more than 6.5 cm, preferably equal to or more than about 7, 8, 9, 10, 11 or 12 cm and/or an average longest branch of equal to or more than 225 cm, e.g. equal to or more than 230 cm, 250 cm, 300 cm, 350 cm or more. Examples are varieties Ace, Jenny, SP-1, SP-4.

An "intermediate vine type" refers to the vegetative type of a plant or plant line or variety which falls between the standard and compact vine type as defined above. It has an average internode length of less than 10.5 cm, e.g. equal to or less than 10, 9, 8, 7, 6 or 5 cm, preferably about 6.0, 6.5, 7.0, 7.5, 8.0, 8.5 or 9.0 cm and/or an average longest branch of equal to or less than about 220 cm. The longest branch is on average preferably about 175-220 cm, e.g. preferably about 175, 180, 185, 190, 195, 200, 205, 210, 215 or 220 cm.

Throughout this document "average" and "mean" are used interchangeably and refer to the arithmetic mean.

A plant having "(essentially) all the physiological and morphological characteristics" means a plant having essentially all or all the physiological and morphological characteristics when grown under the same environmental conditions of the plant of WH 9306, WH9307, WH9308, WH9309, WH9322, WH9313, WH9317, WH9318, WH9319, WH9320, WH9321, WH9716, WH9717, or WH9721 from which it was derived, e.g. the progenitor plant, the parent, the recurrent parent, the plant used for tissue- or cell culture, etc. For example, the plant may have all fruit and/or all flowering characteristics described. In certain embodiments, the plant having "essentially all the physiological and morphological characteristics" are plants having all the physiological and morphological characteristics, except for certain characteristics, such as one, two or three, mentioned, e.g. the characteristic(s) derived from a converted or introduced gene or trait and/or except for the characteristics which differ in an EDV (Essentially Derived Variety). As such, the plant may have all fruit and/or flowering characteristics described, except for one, two or three characteristics described, in which the plant may thus differ. For example, the fruits may have a higher average Brix than in the Examples.

The physiological and/or morphological characteristics mentioned above are commonly evaluated at significance levels of 1%, 5%, 8% or 10% significance level, when measured under the same environmental conditions. For example, a progeny plant of WH 9306, WH9307, WH9308, WH9309, WH9322, WH9313, WH9317, WH9318, WH9319, WH9320, WH9321, WH9716, WH9717, or WH9721 may have one or more (or all, or all except one, two or three) of the essential physiological and/or morphological characteristics of WH 9306, WH9307, WH9308, WH9309, WH9322, WH9313, WH9317, WH9318, WH9319, WH9320, WH9321, WH9716, WH9717, or WH9721, respectively, or one or more or all (or all except one, two or three) of the fruit and/or flowering characteristics, as determined at the 1% or 5% significance level when grown under the same environmental conditions.

The term "traditional breeding techniques" encompasses herein crossing, selfing, selection, double haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce progeny plants. Progeny plants which have the trait are then crossed to the recurrent parent. After several generations of backcrossing and/or selfing the recurrent parent comprises the trait of the donor. The plant generated in this way may be referred to as a "single trait converted plant".

"Progeny" as used herein refers to plants derived from a plant designated WH 9306, WH9307, WH9308, WH9309, WH9322, WH9313, WH9317, WH9318, WH9319, WH9320, WH9321, WH9716, WH9717, or WH9721. Progeny may be derived by regeneration of cell culture or tissue culture or parts of a plant designated WH 9306, WH9307, WH9308, WH9309, WH9322, WH9313, WH9317, WH9318, WH9319, WH9320, WH9321, WH9716, WH9717, or WH9721, or selfing of a plant designated WH 9306, WH9307, WH9308, WH9309, WH9322, WH9313, WH9317, WH9318, WH9319, WH9320, WH9321, WH9716, WH9717, or WH9721, or by producing seeds of a plant designated WH 9306, WH9307, WH9308, WH9309, WH9322, WH9313, WH9317, WH9318, WH9319, WH9320, WH9321, WH9716, WH9717, or WH9721. In further embodiments, progeny may also encompass plants derived from crossing of at least one plant designated WH 9306, WH9307, WH9308, WH9309, WH9322, WH9313, WH9317, WH9318, WH9319, WH9320, WH9321, WH9716, WH9717, or WH9721 with another watermelon plant of the same or another variety or (breeding) line, backcrossing, inserting of a locus into a plant or selecting a plant comprising a mutation or selecting a variant. A progeny is, e.g., a first generation progeny, i.e. the progeny is directly derived from, obtained from, obtainable from or derivable from the parent plant by, e.g., traditional breeding methods (selfing and/or crossing) or regeneration. However, the term "progeny" generally encompasses further generations such as second, third, fourth, fifth, sixth, seventh or more generations, i.e., generations of plants which are derived from, obtained from, obtainable from or derivable from the former generation by, e.g., traditional breeding methods, regeneration or genetic transformation techniques. For example, a second generation progeny can be produced from a first generation progeny by any of the methods mentioned above. Especially progeny of WH 9306, WH9307, WH9308, WH9309, WH9322, WH9313, WH9317, WH9318, WH9319, WH9320, WH9321, WH9716, WH9717, or WH9721 which are EDVs or which retain all (or all except 1, 2 or 3) physiological and/or morphological characteristics of WH 9306, WH9307, WH9308, WH9309, WH9322, WH9313, WH9317, WH9318, WH9319, WH9320, WH9321, WH9716, WH9717, or WH9721, or which retain all (or all except 1, 2, or 3) of the fruit characteristics and/or flowering characteristics of WH 9306, WH9307, WH9308, WH9309, WH9322, WH9313, WH9317, WH9318, WH9319, WH9320, WH9321, WH9716, WH9717, or WH9721 are encompassed herein.

The terms "gene converted" or "conversion plant" in this context refer to watermelon plants which are developed by backcrossing wherein essentially all of the desired morphological and physiological characteristics of parent are recovered in addition to the one or more genes transferred into the parent via the backcrossing technique or via genetic engineering. Likewise a "Single Locus Converted (Conversion) Plant" refers to plants which are developed by plant breeding techniques comprising or consisting of backcrossing, wherein essentially all of the desired morphological and physiological characteristics of a watermelon variety are recovered in addition to the characteristics of the single locus having been transferred into the variety via the backcrossing technique and/or by genetic transformation.

The term a "cell culture" refers to the cells obtained by culturing of cells derived from plant of the invention. Plant cell cultures are typically grown as cell suspension cultures in a liquid medium or as callus cultures on a solid medium. The culturing of undifferentiated plant cells and calli requires the proper balance of the plant growth hormones like e.g. auxin and cytokinin.

(Plant) Tissue culture is the growth of tissues or cells separate from the organism. This is typically facilitated via use of a liquid, semi-solid, or solid growth medium, such as broth or agar.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for watermelon described herein. The mean, if not indicated otherwise within this application, refers to the arithmetic mean of measurements on at least 3, or at least 5, 8, or 10 different, randomly selected plants or plant parts of a variety or line.

"Substantially equivalent" or "not significantly different" or "not significantly differ" refers to a characteristic that, when compared, does not show a statistically significant difference (e.g., $p \geq 0.05$ using ANOVA) from the mean. Vice versa, "significantly different" or "statistically significantly different" refers to a characteristic that, when compared, does show a statistically significant difference (e.g., $p < 0.05$ using ANOVA) from the mean.

DETAILED DESCRIPTION OF EMBODIMENTS OF THE INVENTION

Figure 1:
FIG. 1 shows fruits of exemplary pollenizers according to the invention and described in Example 2.
Figure 2:
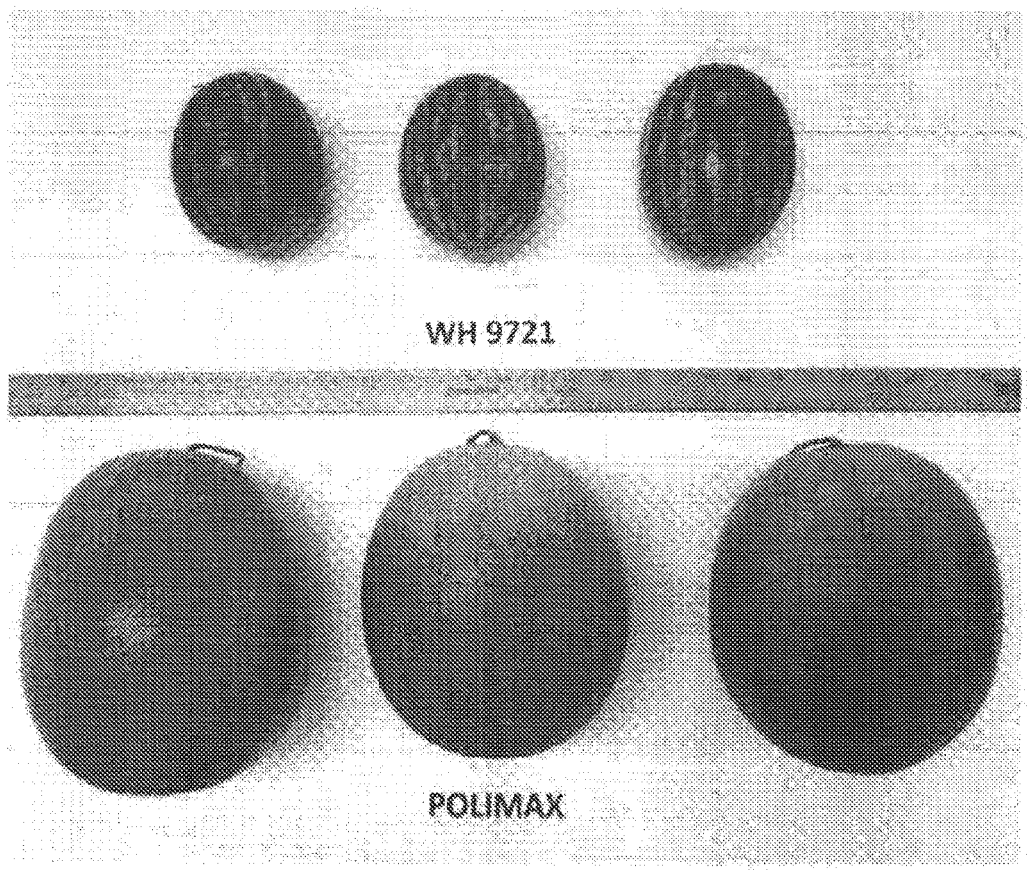
FIG. 2 shows exemplary pollenizers according to the invention and described in Example 5.

The invention provides plants (and seeds from which such plants are grown) of the species Citrullus lanatus, wherein said plant is suitable as a pollenizer in triploid watermelon production, is diploid and produces marketable diploid fruits having an average weight of less than 2.0 kg, preferably less than 1.8 kg, more preferably equal to or less than 1.7, 1.6, 1.5, 1.4, 1.3, 1.2, 1.0 kg, more preferably equal to or less than 0.9, 0.8, 0.7, 0.65 kg, such as equal to or less than 0.6, 0.5, 0.4, 0.35, 0.3 or 0.25 kg at harvest (i.e. at maturity). In a further embodiment average fruit size is equal to or less than about 0.9 kg (such as 0.8, 0.7, 0.65, 0.6, 0.5, 0.4 kg) but above 0.25 kg. To determine average fruit characteristics, such as average fruit weight, of a plant line or hybrid according to the invention several plants of a line or hybrid are grown in one location and 3, 4, 5 or more fruits are harvested from 2, 3, or more plants of the same line and e.g. weighed. Reference plant lines (such as known pollenizers) can be grown at the same location (e.g. in the same trial or under the same environmental conditions) as a comparison. The average fruit weight according to the invention is in one embodiment preferably less than 0.65 kg, more preferably equal to or less than about 0.6, 0.5, 0.4, 0.3 or 0.25 kg. In another embodiment the average fruit size is less than 0.65 kg but above 0.25 kg.

Fruit diameters can be variable, but preferably average fruit length is less than 12 cm, more preferably equal to or less than about 11.5 or 11 cm, such as equal to or less than 10.5, 10.0, 9.5, 9.0, 8.5 or 8.0 cm, while the average fruit width is preferably less than 11, 10.5 or 10 cm, such as equal to or less than 9.5, 9.0, 8.5, 8.0 cm. Thus, average fruit dimensions range have ranges of 8.0-12.0 cm average length×8.0-11 cm average width. Preferably at least fruit length is on average below 12 cm, preferably below 11.5 cm, more preferably about 11 cm or less. Preferably, both length and width of the fruits is on average about 11 cm or less. In one embodiment the average length by width is 10×11 cm, or less. In one embodiment average fruit dimensions for both lengths and width are equal to or below 10.5 cm. These dimensions are particularly encompassed for the diploid fruit weights of less than 0.65 kg on average. For the heavier diploid fruits (e.g. less than 1.8 kg but above 0.65 kg) also larger dimensions are encompassed herein, such as an average length of equal to or less than 17 cm (such as 16, 15, 14, 13, 12 cm) and an average width of equal to or less than 15 cm, such as 14, 13, 12 cm).

The fruits, i.e. the fruit flesh, produced on the pollenizer plants are edible at maturity. The flesh color of the mature fruits of the diploid plants according to the invention is in one embodiment red, having an RHS mini color chart value (Royal Horticultural Society mini color chart) of 39 or higher, especially between 39 and 41. Especially fruits with flesh colors RHS 39B, 41A, 41B, 42 A, 42B, 43A, 43B, 44A, 44B are encompassed. Also, the average percent Total Soluble Solids (% TTS; herein also referred to as degrees Brix, or ° Brix) of the fruits is at maturity at least about 7.5%, preferably at least about 8% or 8.5%, more preferably at least about 9% or 9.5%, and even more preferably at least about 10%, 10.5%, 11%, 11.5%, 12%, 12.5%, 13%, or more. Average TSS can, for example, be determined using a refractometer as described in the Examples. The average percentage TSS of the diploid fruits produced by the pollenizer plants according to the invention can be increased by traditional breeding techniques, e.g. by crossing the plants provided herein with watermelon plants comprising high TSS and selection of progeny (e.g. obtainable by one or more selfings and/or backcross populations) producing fruits with higher TSS values while maintaining small fruit size.

As mentioned, the diploid fruits according to the invention are edible, i.e. they have fruit quality characteristics which make them marketable for human consumption. This means that the fruits have good flavor properties (no off-flavors etc.). For fruits to have at least good flavor properties a minimum average brix of at least about 7.5 degrees is desired. Flavor properties can be determined and scored (e.g. as bad, good, very good) by trained test-panels using known methods for evaluating sensory properties of fruits (Karen L. Bett, Ch 13, Fresh-Cut Fruits and Vegetables, Science, Technology, and Market; Edited by Olusola Lamikanra, CRC Press 2002, Print ISBN: 978-1-58716-030-1). Selection for good flavor includes test panels to select against bitterness and other unpleasant flavors, such as caramel flavor. Watermelon checks of varieties which have good flavor properties (e.g. Allsweet, Crimson Sweet) are preferably included in the test.

The fruits should preferably also not be susceptible to what is known as "fruit cracking" and/or should preferably not contain the brittle gene as present in SP-1. The Super Pollenizers such as SP-1 (as described in WO03/075641) bear brittle fruits, which makes the fruits (in particular the fruit flesh) unmarketable as fresh produce (although the seeds contained within the fruits can be harvested and marketed). Crack-resistance is generally selected for during breeding (e.g. in field observations and/or using for example pressure tests or other tests), as cracking is an undesired fruit quality characteristic. See also Haikun et al. 2010, Acta Hort. (ISHS) 871:223-230).

Other fruit characteristics can be introduced by traditional breeding methods (see further below) and thereby combined with pollenizers producing small, edible diploid fruits according to the invention. For example plants can be selected which produce small, edible fruits, as described above, with increased or reduced rind thickness, increased or reduced rind brittleness, various skin/rind colors (e.g. light green; dark green; green-striped with narrow, medium or wide stripes; grey types; with or without spotting; Golden yellow) and rind surfaces (e.g. furrowed or smooth surface), flesh structure/flesh firmness, different fruit shapes (elongate, oval, blocky, spherical or round), higher brix content, higher lycopene and/or vitamin content, different sugar:acid ratios, very good fruit flavor, etc. Also the combination having small edible fruits with another flesh color than red is possible, for example genetic determinants for yellow flesh or orange flesh or white flesh may be introduced, e.g. by backcross breeding with another color-type. See Guner and Wehner 2004, Hort Science 39(6): 1175-1182, in particular pages 1180-1181 describing genes for fruit characteristics. Generally important breeding objectives are early maturity, high fruit yield, high internal fruit quality (good uniform color, high sugar, proper sugar:acid ratio, good flavor, high vitamin and lycopene content, firm flesh texture, non-fibrous flesh texture, freedom from defects such as hollow heart, rind necrosis, blossom-end rot or cross stitch and good rind characteristics and cracking-resistance).

Rind thickness is a characteristic which influences damage during handling and transporting (too thin or too brittle rind), but thin rinds may also be desirable for consumers. For example, when whole fruits are eaten like apples, a thin rind can be desirable. In one embodiment the fruits have a thin rind, such as an average rind thickness (measured on the side) of at least about 0.2 cm, 0.21 cm, 0.22 cm, 0.23 cm, 0.24 cm, 0.25 cm, 0.26 cm, 0.27 cm, 0.28 cm, 0.29 cm, 0.3 cm, 0.4 cm, but less than 0.5 cm, more preferably less than or equal to 0.4 cm, such as 0.2 cm to 0.4 cm. In a preferred aspect the rind is at least 0.2 cm and at most 0.3 cm, preferably between about 0.2 and 0.3 cm. Thus, in one embodiment the rind is thicker than the rind of SP-4 fruit, but thinner than the rind of Polimax, and optionally thinner than the rind of Sidekick fruit. For certain embodiments thicker rinds may be desired and small fruits having a rind of 0.5 or more cm, such as 0.6 and 0.7 cm are also encompassed herein. The rind of the fruits preferably does not crack easily (i.e. is cracking-resistant), both in fruits with thin rinds and thick rinds.

In one embodiment of the invention, the fruits preferably also do not have a brittle rind and/or an explosive rind as described in WO03/075641 on page 13 and 14, i.e. the fruits do not break under pressure in the range of 90 to 140 g/mm$^2$.

Flesh firmness of the diploid fruits is preferably at least about 0.8 (average firmness in kg as in Example 1), more preferably at least about 0.9, 1.0, or more. Flesh firmness can be increased by e.g. crossing with watermelons having firmer fruit flesh and selection for firmer flesh without increasing fruit size. Plants producing fruits with ultra-firm flesh are, for example, described in US2006/0005284.

The diploid plants provided herein are suitable as pollenizers, which means that they produce sufficient pollen at the right time of the day and for an appropriate period of time to induce fruit set in triploid hybrids, leading to a (average) triploid fruit yield at least comparable to that obtained when using e.g. Polimax as pollinator. However, the plants according to the invention need not be sold or marketed as pollenizer for triploid fruit production and need not be used as pollenizer in triploid fruit production. They may also be marketed and/or used solely for diploid fruit production on their own.

In one embodiment the pollenizer plants preferably produce a large number of male flowers at the appropriate time during flowering of the triploid hybrids, preferably at least about 35 open male flowers at day 15 and/or at least about 30 open male flowers at day 22 from the first day of flowering, although the number of male flowers is not critical in determining triploid fruit set, as long as sufficient pollen is produced by the available male flowers to lead to good triploid fruit set. As the pollenizer plants are also used for diploid fruit production, also sufficient female flowers must be produced by the pollenizers to ensure their dual purpose.

As can be seen in the Examples (e.g., Example 2, Table 4), many open male and female flowers were present over the 3 week period counted. At the flowering date (the date when more than 50% of the plant in the plot has male/female flowers) the 11 pollenizer lines had on average 12.6 open male and 3.9 open female flowers. Each line generally had significantly more open male flowers than SP-4 and Polimax. At day 15 and 22 from 1st day of flowering all lines produce significantly more open male flowers than Sidekick, SP-4 and Polimax, all having at least 35 open male flowers at day 15 and at least 30 open male flowers at day 22. However, Polimax is a very good pollenizer for triploid hybrids, despite the fact that the number of male flowers is significantly lower than in the hybrids provided in the Examples. Polimax had only about 18 open male flowers at day 15 and day 20. The pollenizers according to the invention, therefore, may have a lower number of male flowers than in Examples (e.g., Example 2, Table 4), e.g. plants having about the same number of open male flowers as Polimax are encompassed herein, i.e. pollenizers having at least about 15, 18, 20, 25, 30, or more open male flowers at day 15 and/or at day 22 from the 1st day of flowering are also an embodiment of the invention.

Also the number of open female flowers was good, indicating that the pollinizers are indeed suitable for dual-purposes, i.e. pollination and fruit production of triploid hybrids and/or pollination and fruit production on the diploid plants themselves (fruits produced by self-pollination of the pollenizer plant).

In one embodiment of the invention the pollenizer plants are dual purpose pollenizer plants. In particular, the average number of open male flowers at day 22 from flowering is at least 15, 18, 20, 25 or 30 or more.

In one embodiment the pollenizer plants according to the invention are hybrid diploids (F1 diploids) and not open pollinated (OP).

In yet a further embodiment of the invention, the dual purpose pollenizer plants are not of the "edible seed watermelon" or "confectionary" type, as for example produced in variety San Juan (Native Seeds). These types of watermelon are produced to harvest the seeds for consumption or seed oil production and the fruits produce large, black or red edible seeds with soft seed coats, see e.g. Zhang 1996, Cucurbit Genetics Cooperative Report 19:66-67 (article 24) and Zhang and Wang, 1990, Cucurbit Genetics Cooperative Report 13:43-44 (article 16). In contrast, the seeds produced in the diploid fruits according to the invention are small (preferably tomato seed size to medium seed size, but not large) and are not suitable for seed harvest and seed consumption. In one embodiment of the invention the seeds of the diploid fruits are on average shorter than or equal to 5 mm in length, for example shorter than or equal to 4 mm, 3.5 mm, 3 mm, 2.5 mm, 2 mm, 1.5 mm or 1 mm in length.

The dual purpose pollenizer plants not only produce very small, edible fruits, but also high numbers of marketable fruits. In one embodiment a plant according to the invention produces at maturity on average at least about 10, 11, 12, 13, 14, 15, 16, 17, 18, 19, 20 or more fruits per plant, more preferably at least 25 fruits, more preferably at least about 27, 28, 29, 30, 35, 40, 50, 60, 65 or more fruits.

The pollenizer plants according to the invention can be combined with different vine types, such as compact vine type, standard vine type or, most preferably an "intermediate" vine type using normal breeding techniques. For example the pollenizers according to the invention may be crossed with a standard vine type and progeny may be selected which have an intermediate vine type.

It is understood that it is also an object of the invention to provide seeds from which the pollenizer plants described herein can be grown. Also seedlings, scions and rootstocks, as well as cells and tissues of the pollenizer plants are encompassed herein. Such plant parts comprise the genetic determinants for producing dual purpose pollenizer plants according to the invention. Thus whole plants obtained from seedlings, scions and rootstocks, as well as cells and tissues of the pollenizer plants retain all the physiological and morphological characteristics of the pollenizer plants according to the invention when grown under the same environmental conditions.

It is a further object of the invention to provide a plurality of diploid watermelon fruits obtainable on a pollenizer plant according to the invention as described above, and/or seeds present in those fruits. Thus, in one embodiment, harvested diploid fruits are provided, such as packaged whole fruits or fruit parts and/or processed fruits or fruit parts.

Also progeny of the plants according to the invention are provided herein, such as seeds obtainable by crossing a pollenizer plant described herein with another watermelon plant and/or by selling a plant according to the invention to produce F1 seeds (and F1 plants grown from these seeds, as well as fruit produced by self-pollinating the F1 plants).

Further provided are plant cells, cell cultures or tissue cultures of plants according to the invention, as well as root stocks, scions, transplants and vegetative propagations of plants according to the invention or of progeny thereof.

In one aspect, a representative sample of seeds of the plants according to the invention are deposited under accession number NCIMB 41773 (WH9307) or accession number 42704 (WH9716).

In one aspect a watermelon plant (or a seed from which the plant can be grown), or fruit and/or seed thereof, or part of the plant, having essentially all morphological and physiological fruit characteristics and/or flowering characteristics of the plants of which representative samples of seeds have been deposited are provided.

In another aspect a watermelon plant (or a seed from which the plant can be grown), or fruit and/or seed thereof, or part of the plant, having essentially all morphological and physiological characteristics of the plants of which representative samples of seeds have been deposited are provided.

Plants having the genetic determinants for producing small, edible fruits are, therefore, obtainable from the deposited seeds. The genetic determinants (i.e. the combination of genes) for producing small, edible fruits can be transferred to other watermelon plants, for example to create other diploid pollenizers with this phenotype or other diploids (open pollinated or inbred lines, or hybrid diploids). This can be done by using the pollenizers according to the invention as a parental line in breeding methods, i.e. as male or female parent in a cross with another watermelon plant. Known breeding methods can be used alone or in combination, such as (but not limited to) recurrent selection, pedigree breeding, backcross breeding, inbred development, hybrid testing, marker assisted breeding, etc. Diploids may also be used for tetraploid development, using e.g. colchicine treatment. Progeny are then selected which retain the small fruit dimensions and fruit weight, a brix of at least 7.5% and dual purpose pollenizer characteristics, all as described herein.

Other watermelon plants may be used as a starting point to develop dual purpose pollenizer plants producing small, edible fruits according to the invention. For example, small fruited cultivars or lines may be used as starting material, such as for example Sidekick (U.S. Pat. No. 7,314,979) and/or SP-1 (WO 03/075641) and/or watermelon plants carrying the "tomato seed" mutant (gene ts) described in Guner and Wehner (2004, HortScience 39(6):1175-1182) and obtainable from gene curator of the Cucurbit Genetics Cooperative), and selecting for fruit quality characteristics (e.g. high brix, good flavor), small fruit size (e.g. small fruit dimensions and e.g. less than 0.9 kg weight) and small seed size in the diploid fruits, as well as pollenizer characteristics (e.g. many male flowers) as described herein.

Selection for small seed size encompasses selecting for an average seed length of equal to or less than 8 mm, preferably 7 mm, 6 mm or more preferably equal to or less than 5.0 mm, preferably equal to or less than 4.5 mm, e.g. equal to or less than about 4.0 mm, 3.5 mm, 3.0 mm, 2.5 mm or 1.5 mm or 1.0 mm seed length.

In one embodiment a breeding method for producing diploid dual purpose pollenizers according to the invention is provided, comprising:
 a) providing a breeding population of diploid watermelon plants, and
 b) selecting progeny for small fruit size, small seed size, high brix, good flesh color and pollenizer characteristics (all as described throughout this application).

Plants obtainable by this method are encompassed herein. As mentioned, the breeding population can be provided by using at least one, preferably two small-fruited parents and crossing these, to generate an F1 and further progeny generations (F2, etc.). For example, one of the plants provided herein (e.g. WH9307) is used in step a) and is crossed to another watermelon plant. The progeny generations are then selected for at least the characteristics described in b).

In one embodiment one or more hybrid plants is provided, obtained from crossing a pollenizer plant according to the invention with another watermelon plant and harvesting the F1 seeds of said cross. The F1 seeds may then be grown into F1 plants and self-pollinated or sib-pollinated to produce F2 seeds. If the parents used in the initial cross differ by one or more characteristics (e.g. disease resistance and fruit size), the F2 population will segregate for these trait(s) and the breeder can select plants in this and/or further progeny generations (F3, F4, etc.) which combine the desired traits (e.g. small fruit size and disease resistance). Alternatively, the F1 may be backcrossed to the recurrent parent (e.g. the pollenizer according to the invention into which a trait is to be introduced) or the F1 may be selfed to produce an F2 population segregating for the trait of interest and selected F2 plants having the trait of interest may be backcrossed to the recurrent parent.

Thus, one or more traits not present in the pollenizer plants according to the invention can be introduced into a pollenizer plant according to the invention, while maintaining the genetic determinants for small diploid fruits. For example other fruit characteristics as described above can be introduced (e.g. darker red flesh color, higher brix, firmer flesh, a different flesh color, etc.), or any other traits can be introduced, such as one or more QTLs for high yield, disease resistance genes, stress tolerance genes (e.g. water stress tolerance), etc. resistance to fungal-, bacterial-, viral-diseases, root-knot nematodes and/or insect pests may be introduced. For example, resistance to *Fusarium* wilt (*Fusarium oxysporum* fsp. *niveum* race 0, race 1 and/or race 2, and/or race 3, and/or other new races which may develop), Anthracnose (*Colletotrichum lagenarium* races 1-7, or other new races), Gummy stem blight, powdery mildew, *Verticillium* wilt, bacterial fruit blotch, papaya ringspot virus (PRSV), watermelon mosaic virus (WMV) or zucchini yellow mosaic virus (ZYMV).

Resistance to *Fusarium* wilt races 0 and 1 is present in many commercial varieties, and also resistance to race 2 has been identified in PI296341 and PI271769 and is also present in SP-4 (U.S. Pat. No. 7,550,652). Anthracnose resistance to race 1 is for examples present in SP-4 and resistance to race 2 in AU-Sweet Scarlet (AW-82-50CS) (Breeder: Alabama Agric. Expt. Station, Auburn University). Crimson Sweet has the Ar-1 gene, which provides resistance to anthracnose races 1 and 3. Gummy stem blight resistance is also found in Plant Introduction lines.

Also provided is a method for producing diploid and triploid watermelon fruits in one field, said method comprising:
 (a) interplanting diploid pollenizer plants according to the invention and triploid hybrid plants in one field,
 (b) allowing pollination of flowers of the triploid hybrid plants with pollen of the diploid pollenizer plants and allowing pollination of flowers of the diploid pollenizer plants with pollen of the diploid pollenizer plants,
 (c) harvesting fruits produced on the triploid hybrid plants and, optionally, harvesting fruits produced on the diploid pollenizer plants.

In one embodiment of the invention the diploid fruits and/or the triploid fruits are edible and red-fleshed, white-fleshed, orange-fleshed or yellow-fleshed.

In a further embodiment the rind of the diploid fruits is not yellow or Golden (as controlled by the recessive gene go) (Barham 1965, Proc Ameri Soc Hort Sci 67: 487-489).

Interplanting in one field may be either done by seeding or transplants of the pollenizer and triploids. Various interplanting methods can be used, as known in the art and various ratios of pollenizer:triploid hybrid may be used. One row of pollenizer plants may for example be present at least every 2, at least every 3 or at least every 4 rows of triploids, but other methods of interplanting may also be used.

Any triploid hybrid may be used, such as known triploid hybrid varieties.

Pollination is usually done by bees, and bee hives can be provided to the fields unless sufficient wild bees are naturally present. Pollination can also be performed by manual or mechanical means. Harvest at maturity may be done by hand or mechanized.

The diploid fruit may be distinguished from the triploid fruit based on the smaller fruit size of the diploid fruit, and/or alternatively by a different rind pattern. In one embodiment the rind of the diploid fruits according to the invention is not yellow or golden. Preferably harvested diploid and triploid fruit are placed into different containers. Thus, in one embodiment a container comprising solely small diploid fruits according to the invention is provided. Any type of container may be used, e.g. cartons, boxes, etc.

Also a method for producing small diploid edible watermelon fruits having an average weight of less than 1.8 kg, 1.7 kg, 1.0 kg, 0.9 kg, 0.8 kg, 0.7 kg, preferably equal to or less than 0.65 kg (but in one embodiment larger than 0.25 kg), is provided comprising:
 (a) growing a plant according to the invention, i.e. a pollenizer as described herein,
 (b) pollinating the female flowers of said plant with pollen of said plant,
 (c) harvesting the fruits produced on said plant.

Thus, by self-pollination of a diploid plant according to the invention, small edible diploid fruits are produced. The pollenizers according to the invention may be grown in a field without other watermelon plants being present, and the small diploid fruits may be harvested and placed in containers for transport. Step (b) may be performed by allowing insect pollination or any other means of pollinating.

In one embodiment a diploid pollenizer plant (or a seed from which the plant can be grown) capable of producing small edible diploid fruits having an average weight of less than 1.8 kg, 1.7 kg, 1.0 kg, 0.9 kg, 0.8 kg, 0.7 kg or equal to or less than 0.65 kg (but in one embodiment larger than 0.25 kg) is provided, wherein a representative sample of seed containing the genetic elements for producing said small fruits has been deposited under accession number NCIMB 41773 (WH9307) or accession number 42704 (WH9716).

Especially, pollenizer hybrid WH 9307 comprises the genetic elements for producing said small, edible fruits according to the invention and a representative sample of seeds have been deposited under accession number NCIMB 41773. Thus, when referring herein to seed deposits of pollenizers according to the invention, this pollenizer is referred to as a representative plant according to the invention, but seeds of the other hybrids or lines are also suitable and when reference to WH9307 or progeny thereof (or parts of any of these) is made, the other hybrids or lines mentioned herein are equally implied.

In one embodiment a hybrid watermelon seed is provided, having as a male or female parent (preferably as a male parent) a diploid pollenizer plant capable of producing small edible diploid fruits having an average weight of less than 1.8 kg, 1.7 kg, 1.0 kg, 0.9 kg, 0.8 kg, 0.7 kg or equal to or less than 0.65 kg (but in one embodiment larger than 0.25 kg) is provided, wherein a representative sample of seed containing the genetic elements for producing said small diploid fruits has been deposited under accession number NCIMB 41773 (WH9307) or accession number 42704 (WH9716).

In one embodiment the fruit of a cross-pollination between a diploid pollenizer plant as pollen donor capable of producing small diploid fruits having an average weight of less than 1.8 kg, 1.7 kg, 1.0 kg, 0.9 kg, 0.8 kg, 0.7 kg or equal to or less than 0.65 kg (but in one embodiment larger than 0.25 kg) is provided, wherein a representative sample of seed containing the genetic elements for producing said small fruits has been deposited under accession number NCIMB 41773 (WH9307) or accession number 42704 (WH9716) and the pistillate flowers of another watermelon plant is provided. The other watermelon plant is preferably a triploid hybrid and the fruit is triploid and preferably seedless.

In one embodiment a diploid fruit and/or an inbred diploid seed is provided produced by self-pollinating a diploid pollenizer plant capable of producing small edible diploid fruits having an average weight of less than 1.8 kg, 1.7 kg, 1.0 kg, 0.9 kg, 0.8 kg, 0.7 kg or equal to or less than 0.65 kg (but in one embodiment larger than 0.25 kg) is provided, wherein a representative sample of seed containing the genetic elements for producing said small diploid fruits has been deposited under accession number NCIMB 41773 (WH9307) or accession number 42704 (WH9716).

In one aspect of the invention plants according to the invention and fruits according to the invention are obtainable from WH 9306, WH9307, WH9308, WH9309, WH9322, WH9313, WH9317, WH9318, WH9319, WH9320, WH9321, WH9716, WH9717, WH9721 or of progeny of any of these.

Plants obtained (derived), or obtainable (derivable), from plants according to the invention (e.g. from deposited seeds) include, therefore, plants obtained by breeding methods, such as selfing, crossing, backcrossing, recurrent selection, double haploid production, marker assisted selection, clonal propagations, transformants, etc., whereby the derived plants produce small, edible fruits according to the invention.

In another aspect of the invention plants having essentially all the morphological and/or physiological characteristics of WH 9306, WH9307, WH9308, WH9309, WH9322, WH9313, WH9317, WH9318, WH9319, WH9320, WH9321, WH9716, WH9717, WH9721 or of progeny of any of these, are provided. Representative examples of physiological and morphological characteristics are provided in Tables 1-8.

Also provided is a progeny plant of WH 9306, WH9307, WH9308, WH9309, WH9322, WH9313, WH9317, WH9318, WH9319, WH9320 or WH9321, WH9716, WH9717, WH9721 obtained by further breeding with said plant, wherein said progeny plant has essentially all physiological and morphological characteristics of said plant.

A plant comprising a first set of chromosomes of any of the plants WH9716, or WH9717, or WH9721, a representative sample of seeds of WH9716 having been deposited under Accession Number NCIMB 42704.

A seed comprising a first set of chromosomes of any of the plants WH9716, or WH9717, or WH9721, a representative sample of seeds of WH9716 having been deposited under Accession Number NCIMB 42704.

Essentially all physiological and morphological characteristics include herein at least small, edible fruits and dual purpose pollenizer characteristics as described throughout the description and examples. Thus, in one aspect, essentially all physiological and morphological characteristics refer herein to a plant having the fruit characteristics and/or the flowering (pollenizer) characteristics as described in specification and the Examples.

Also a plant part (e.g. a fruit, tissue, cell, cell culture, vegetative propagation, pollen, etc.) is provided which, when regenerated or grown into a whole plant, has essentially all the morphological and/or physiological characteristics of WH 9306, WH9307, WH9308, WH9309, WH9322, WH9313, WH9317, WH9318, WH9319, WH9320 or WH9321, WH9716, WH9717, WH9721.

Also provided is a plant derived from (or obtained from) or derivable from (or obtainable from) any of WH 9306, WH9307, WH9308, WH9309, WH9322, WH9313, WH9317, WH9318, WH9319, WH9320 or WH9321, WH9716, WH9717, WH9721 having one or two physiological and/or morphological characteristics which are different from the WH plant listed and which otherwise has essentially all physiological and morphological characteristics of a plant designated WH 9306, WH9307, WH9308, WH9309, WH9322, WH9313, WH9317, WH9318, WH9319, WH9320 or WH9321, WH9716, WH9717, WH9721 obtainable by further breeding with the WH plant and/or by selecting a natural or induced mutant, or a somaclonal variant from a population of plants designated WH 9306, WH9307, WH9308, WH9309, WH9322, WH9313, WH9317, WH9318, WH9319, WH9320 or WH9321 WH9716, WH9717, WH9721.

Thus, the invention provides a seed of watermelon variety WH 9306, WH9307, WH9308, WH9309, WH9322, WH9313, WH9317, WH9318, WH9319, WH9320, WH9321, WH9716, WH9717, or WH9721.

The invention provides a plant of watermelon variety WH 9306, WH9307, WH9308, WH9309, WH9322, WH9313, WH9317, WH9318, WH9319, WH9320, WH9321, WH9716, WH9717, or WH9721, or a part thereof.

The invention provides a fruit of watermelon variety WH 9306, WH9307, WH9308, WH9309, WH9322, WH9313, WH9317, WH9318, WH9319, WH9320, WH9321, WH9716, WH9717, or WH9721, or a plant part produced from the plant above.

The invention provides a method of producing a watermelon plant, comprising crossing any one of the plants of WH 9306, WH9307, WH9308, WH9309, WH9322, WH9313, WH9317, WH9318, WH9319, WH9320, WH9321, WH9716, WH9717, or WH9721 with a second watermelon plant one or more times, and selecting progeny from said crossing.

The invention provides a method of producing a watermelon plant, comprising selling any one of the plants of WH 9306, WH9307, WH9308, WH9309, WH9322, WH9313, WH9317, WH9318, WH9319, WH9320, WH9321, WH9716, WH9717, or WH9721 one or more times, and selecting progeny from said selling.

The invention provides progeny of watermelon variety WH 9306, WH9307, WH9308, WH9309, WH9322, WH9313, WH9317, WH9318, WH9319, WH9320, WH9321, WH9716, WH9717, or WH9721 obtained by further breeding with said variety.

The invention provides the progeny of watermelon variety WH 9306, WH9307, WH9308, WH9309, WH9322, WH9313, WH9317, WH9318, WH9319, WH9320, WH9321, WH9716, WH9717, or WH9721, wherein said progeny have all the physiological and morphological fruit and/or flowering characteristics of watermelon variety WH 9306, WH9307, WH9308, WH9309, WH9322, WH9313, WH9317, WH9318, WH9319, WH9320, WH9321, WH9716, WH9717, or WH9721 respectively when grown under the same environmental conditions.

The invention provides the progeny of watermelon variety WH 9306, WH9307, WH9308, WH9309, WH9322, WH9313, WH9317, WH9318, WH9319, WH9320, WH9321, WH9716, WH9717, or WH9721, wherein said progeny have all the physiological and morphological characteristics of watermelon variety WH 9306, WH9307, WH9308, WH9309, WH9322, WH9313, WH9317, WH9318, WH9319, WH9320, WH9321, WH9716, WH9717, or WH9721, respectively, when grown under the same environmental conditions.

The invention provides an Essentially Derived Variety of any one of WH9306, WH9307, WH9308, WH9309, WH9322, WH9313, WH9317, WH9318, WH9319, WH9320, WH9321, WH9716, WH9717, or WH9721 having one, two or three physiological and/or morphological characteristics which are different from those of WH 9306, WH9307, WH9308, WH9309, WH9322, WH9313, WH9317, WH9318, WH9319, WH9320, WH9321, WH9716, WH9717, or WH9721 and which otherwise has all the physiological and morphological characteristics of WH 9306, WH9307, WH9308, WH9309, WH9322, WH9313, WH9317, WH9318, WH9319, WH9320, WH9321, WH9716, WH9717, or WH9721.

The invention provides a method of producing plants, or a part thereof, of variety WH 9306, WH9307, WH9308, WH9309, WH9322, WH9313, WH9317, WH9318, WH9319, WH9320, WH9321, WH9716, WH9717, or WH9721 comprising vegetative propagation of variety WH 9306, WH9307, WH9308, WH9309, WH9322, WH9313, WH9317, WH9318, WH9319, WH9320, WH9321, WH9716, WH9717, or WH9721, respectively.

In one aspect said vegetative propagation comprises regenerating a whole plant from a part of variety WH 9306, WH9307, WH9308, WH9309, WH9322, WH9313, WH9317, WH9318, WH9319, WH9320, WH9321, WH9716, WH9717, or WH9721.

In one aspect, said part is a cutting, a cell culture or a tissue culture.

The invention provides a vegetative propagated plant of variety WH 9306, WH9307, WH9308, WH9309, WH9322, WH9313, WH9317, WH9318, WH9319, WH9320, WH9321, WH9716, WH9717, or WH9721, or a part thereof, having all the morphological and physiological characteristics of WH 9306, WH9307, WH9308, WH9309, WH9322, WH9313, WH9317, WH9318, WH9319, WH9320, WH9321, WH9716, WH9717, or WH9721, respectively, when grown under the same environmental conditions.

The invention provides a plant part derived from variety WH 9306, WH9307, WH9308, WH9309, WH9322, WH9313, WH9317, WH9318, WH9319, WH9320, WH9321, WH9716, WH9717, or WH9721, or from the vegetatively propagated plant above, wherein said plant part are harvested fruit or parts thereof, pollen, cells, leaves or parts thereof, petioles, shoots or parts thereof, stems or parts thereof, roots or parts thereof, cuttings, or flowers or parts thereof.

The invention provides a food or feed product comprising such a plant part. The plant part is fresh or processed.

The invention provides a watermelon plant produced by growing the seed of WH 9306, WH9307, WH9308, WH9309, WH9322, WH9313, WH9317, WH9318, WH9319, WH9320, WH9321, WH9716, WH9717, or WH9721.

The invention provides a method of producing a watermelon plant having a desired trait, wherein the method comprises transforming the watermelon plant WH 9306, WH9307, WH9308, WH9309, WH9322, WH9313, WH9317, WH9318, WH9319, WH9320, WH9321, WH9716, WH9717, or WH9721 with a transgene that confers the desired trait, wherein the transformed plant retains all the phenotypic and morphological characteristics of variety WH 9306, WH9307, WH9308, WH9309, WH9322, WH9313, WH9317, WH9318, WH9319, WH9320, WH9321, WH9716, WH9717, or WH9721, respectively, and contains the desired trait.

The invention provides a watermelon plant produced by the method above, wherein the plant comprises the desired trait and all of the physiological and morphological characteristics of WH 9306, WH9307, WH9308, WH9309, WH9322, WH9313, WH9317, WH9318, WH9319, WH9320, WH9321, WH9716, WH9717, or WH9721. The invention provides a watermelon plant comprising at least a first set of the chromosomes of watermelon line WH 9306, WH9307, WH9308, WH9309, WH9322, WH9313, WH9317, WH9318, WH9319, WH9320, WH9321, WH9716, WH9717, or WH9721, and further comprising a single locus conversion, wherein said plant has essentially all of the morphological and physiological characteristics of the plant comprising at least a first set of the chromosomes of watermelon line WH 9306, WH9307, WH9308, WH9309, WH9322, WH9313, WH9317, WH9318, WH9319, WH9320, WH9321, WH9716, WH9717, or WH9721.

The single locus conversion in one aspect confers a trait of male sterility, herbicide tolerance, insect resistance, pest resistance, disease resistance, environmental stress tolerance, modified carbohydrate metabolism, modified protein metabolism, or any combination thereof.

The invention also provides use of any one of WH 9306, WH9307, WH9308, WH9309, WH9322, WH9313, WH9317, WH9318, WH9319, WH9320, WH9321, WH9716, WH9717, or WH9721, or progeny of any one of these, for providing pollen to produce triploid, seedless watermelon fruits.

The invention thus also provides triploid fruits produced from one of WH 9306, WH9307, WH9308, WH9309, WH9322, WH9313, WH9317, WH9318, WH9319, WH9320, WH9321, WH9716, WH9717, or WH9721, or progeny of any one of these, as male parent (pollenizer) and a triploid watermelon plant as female parent.

DEPOSIT INFORMATION

Applicant(s) maintain a deposit of at least 2500 seeds of hybrid pollenizers mentioned in the Examples, and parent inbred lines, at Nunhems B. V. Applicant has deposited hybrid WH 9307 at the NCIMB on 12 Nov. 2010 under Accession number NCIMB 41773, and WH 9716 at the NCIMB on 12 Dec. 2016 under Accession number NCIMB 42704. Access to this deposit will be available during the pendency of this application to persons determined by the Commissioner of Patent and Trademarks to be entitled thereto upon request.

Subject to 37 C.F.R. §1.808(b), all restrictions imposed by the depositor on the availability to the public of one or more deposits will be irrevocably removed upon the granting of the patent by affording access to a deposit of at least 2500 seeds with the American Type Culture Collection (ATCC), 10801 University Boulevard, Manassas, Va. 20110 or National Collections of Industrial, Food and Marine Bacteria (NCIMB), 23 St. Machar Drive, Aberdeen, Scotland, AB24 3RY, United Kingdom. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The following non-limiting Examples describe the production of diploid pollenizers and small, edible diploid fruits according to the invention. Unless stated otherwise in the Examples, methods for conventional watermelon breeding are used, such as e.g. described in Maynard 2001, Watermelons—Characteristics, Production and Marketing, ASHS Press; Mohr H. C. Watermelon Breeding in Mark J. Bassett (editor) 1986 Breeding Vegetable Crops, AVI Publishing Company.

EXAMPLES

Example 1—Breeding History

Breeding for the hybrids goes back to 1985, to in-house breeding lines and crosses of these with the variety Allsweet. Selected self-pollinations were backcrossed with Tomato Seed OP (Sugar Baby mutant; ts gene) and selections were made for red flesh and small seed. Further self-pollinations were selected for red flesh, small seeds and agronomic traits in general. Selections were crossed with a line with many male flowers, followed by several selfings and selection for the production of many male flowers and small red fruits.

Example 2—Pollenizer Characteristics 2.1—Materials and Methods

A field trial was conducted in Italy (Sant'Agata Bolognese-BO). Seeds were sown on 7 Apr. 2010 and transplanted into the field on 21 May 2010 (100 cm within the row, 250 cm between the rows). The plot contained 10 plants per line. Fruits were harvested on 26/27 Jul. 2010 for evaluation.

2.1.1 Flowering

The number of open male and female flowers were counted for three plants per line on the flowering date (day 1=24 Jun. 2010), and 8, 15 and 22 days after the flowering date (day 8=2 Jul. 2010; day 15=9 Jul. 2010; day 22=16 Jul. 2010). The mean number of three plants per line was calculated.

2.1.2 Fruits

1) Average fruit number: at maturity (26/27 July) the total number of fruits harvested from two plants was counted and the average fruit number determined.

2) Average fruit weight: mean of the weight of three fruits per line randomly harvested from two plants at maturity 3) Brix: Value is the mean of three reading for three fruit, collected between the centre and the rind of the fruit; expressed in Degrees Brix)(° using the K71901 portable refractometer Mod. RLC ATC 0-18% (OPTECH).

4) Flesh structure (flesh firmness): Value is the mean of the reading of three fruits; expressed in kg using the fruit pressure tester FT 011 (Cientec Instrumentos)

5) Flesh colour: evaluated using the Royal Horticultural Society mini colour chart (http://www.rhs.org.uk/Plants/RHS-Publications/RHS-colour-charts)

2.1.3 Other Fruit Characteristics

Measurements were done for three fruits:

1) Fruit length (cm), indicated as FRT-cm_L

2) Fruit diameter at midsection (cm), indicated as FRT-cm_D

3) Fruit rind thickness (cm), blossom end, indicated as RND-cm_BE

4) Fruit rind thickness (cm), side of fruit, indicated as RND-cm_S.

Rind thickness is measured from the outer edge of the fruit to the boundary between white mesocarp and colored endocarp.

2.2—Results
2.2.1—Fruit Characteristics

TABLE 1

Fruit characteristics of fruits from 11 diploid pollenizers according to the invention and commercial diploid pollenizers (Sidekick, SP-4 and Polimax)

| Dual Purpose Pollenizers (diploid hybrids) | Average fruit no. | Average fruit weight (kg) | °Brix | Fruit flesh structure (kg) | Flesh color (RHS) |
|---|---|---|---|---|---|
| WH 9306x | 38.5 | 0.52 | 7.0 | 0.6 | Red (41A) |
| WH 9307x | 41.0 | 0.55 | 8.5 | 1.4 | Red (41A) |
| WH 9308x | 51.0 | 0.44 | 7.7 | 0.6 | Red (41B) |
| WH 9309x | 38.5 | 0.45 | 8.0 | 0.6 | Red (41A) |
| WH 9311x | 56.5 | 0.55 | 7.3 | 0.6 | Red (41B) |
| WH 9313x | 23.5 | 0.59 | 6.3 | 0.5 | Red (39B) |
| WH 9317x | 51.5 | 0.45 | 5.7 | 0.6 | Red (41B) |
| WH 9318x | 34.5 | 0.51 | 7.7 | 0.6 | Red (39B) |
| WH 9319x | 52.5 | 0.57 | 7.3 | 0.6 | Red (39B) |
| WH 9320x | 35.5 | 0.49 | 7.7 | 0.5 | Red (41B) |
| WH 9321x | 49.5 | 0.33 | 6.2 | 0.5 | Red (39B) |
| Min-Max | 23.5-56.5 | 0.33-0.59 | 5.7-8.5 | 0.5-1.4 | Red (RHS 39B-41A) |
| (average) | (43.0) | (0.49) | (7.2) | (0.6) | |
| Commercial pollenizers: | | | | | |
| Sidekick | 27.5 | 0.75 | 7.7 | 0.6 | Pink (31D) |
| SP-4 | 8.5 | 1.4 | 5.2 | 1.1 | white |
| Polimax | 5.0 | 2.3 | 10.3 | 1.0 | red |

As can be seen from Table 1, the diploid pollenizers according to the invention produced very small, red-fleshed edible fruits. Fruit weight in Table 1 is significantly smaller than that of commercial pollenizers such as Sidekick, SP-4 and Polimax.

TABLE 2

Fruit dimensions

| Pollenizers (diploid hybrids) | Average length (cm) (FRT-cm_L) | Average width (cm) (FRT-cm_D) |
|---|---|---|
| WH 9306x | 11.33 | 10.17 |
| WH 9307x | 10.50 | 9.83 |
| WH 9308x | 10.50 | 9.67 |
| WH 9309x | 11.00 | 10.00 |
| WH 9311x | 10.38 | 9.88 |
| WH 9313x | 11.33 | 10.00 |
| WH 9317x | 10.83 | 9.17 |
| WH 9318x | 11.17 | 9.67 |
| WH 9319x | 10.67 | 9.33 |
| WH 9320x | 11.33 | 9.17 |
| WH 9321x | 9.67 | 8.67 |
| Commercial pollenizers: | | |
| Sidekick | 12.00 | 11.33 |
| SP-4 | 15.33 | 13.17 |
| Polimax | 16.50 | 16.00 |

Table 2 shows that the pollenizers according to the invention have on average smaller fruit dimensions than the commercial pollenizers. The fruit length is on average 11.33 cm or smaller, while in Sidekick the average fruit length is 12 cm. The diameter is also smaller, only 10.17 cm or less, compared to 11.33 cm in Sidekick. Thus fruit dimensions of equal to or below 11.33×10.17 cm (e.g. even as small as 9.67×8.67 cm) are significantly smaller than 12.00×11.33 cm in Sidekick.

Table 3 shows mean rind thicknesses per line, measured at two points of the fruit. Thin rinds are an advantage for consumption.

TABLE 3

Rind thickness at the blossom end and on the side of the fruit

| Pollenizers (diploid hybrids) | Average rind thickness - blossom end (cm) (RND-cm_BE;) | Average rind thickness - side (cm) (RND-cm_S) |
|---|---|---|
| WH 9306x | 0.17 | 0.37 |
| WH 9307x | 0.27 | 0.43 |
| WH 9308x | 0.20 | 0.37 |
| WH 9309x | 0.20 | 0.40 |
| WH 9311x | 0.25 | 0.40 |
| WH 9313x | 0.23 | 0.47 |
| WH 9317x | 0.15 | 0.33 |
| WH 9318x | 0.20 | 0.30 |
| WH 9319x | 0.23 | 0.40 |
| WH 9320x | 0.20 | 0.40 |
| WH 9321x | 0.13 | 0.30 |
| Commercial pollenizers: | | |
| Sidekick | 0.30 | 0.43 |
| SP-4 | 0.10 | 0.10 |
| Polimax | 0.40 | 0.70 |

The pollenizers according to the invention have good, although thin, rind thickness of between 0.30 and 0.47 cm. The rind is also not susceptible to cracking, giving the fruits good handling properties. Fruits do also not have a brittle or explosive rind.

The rind pattern of the fruits of all pollenizers according to the invention is a Crimson Sweet type rind pattern (medium-striped or netted), but the small fruit size can also be combined with other rind colors using standard breeding methods.

2.2.2—Flowering Characteristics

TABLE 4

Flowering characteristics of 11 diploid pollenizers according to the invention and commercial diploid pollenizers (Sidekick, SP-4 and Polimax)

| | No. of open male flowers | | | | No. of open female flowers | | | |
|---|---|---|---|---|---|---|---|---|
| | Day 1 | Day 8 | Day 15 | Day 22 | Day 1 | Day 8 | Day 15 | Day 22 |
| Pollenizer | | | | | | | | |
| WH 9306x | 18.3 | 48.3 | 49.0 | 35.7 | 4.7 | 2.0 | 0.0 | 1.3 |
| WH 9307x | 15.0 | 51.0 | 53.7 | 35.0 | 4.7 | 3.0 | 0.3 | 1.0 |
| WH 9308x | 12.3 | 45.0 | 36.0 | 41.7 | 4.3 | 4.7 | 0.0 | 2.0 |
| WH 9309x | 10.0 | 42.3 | 49.7 | 46.7 | 2.0 | 1.0 | 0.3 | 2.3 |
| WH 9311x | 11.7 | 54.7 | 57.0 | 61.7 | 1.3 | 6.3 | 0.7 | 3.0 |
| WH 9313x | 9.0 | 57.3 | 47.7 | 40.3 | 5.0 | 2.7 | 0.3 | 1.3 |
| WH 9317x | 12.0 | 56.7 | 68.3 | 82.3 | 5.0 | 4.7 | 0.7 | 5.3 |
| WH 9318x | 7.0 | 38.7 | 65.3 | 68.7 | 4.7 | 5.7 | 0.0 | 5.3 |
| WH 9319x | 18.3 | 71.7 | 54.3 | 56.7 | 3.7 | 3.3 | 0.3 | 1.3 |
| WH 9320x | 12.0 | 43.7 | 47.7 | 33.3 | 3.3 | 2.0 | 0.0 | 0.7 |
| WH 9321x | 13.3 | 42.7 | 65.0 | 56.7 | 4.3 | 5.3 | 0.0 | 3.3 |
| Min-Max | 7.0-13.8 | 38.7-71.7 | 36.0-68.3 | 33.3-82.3 | 1.3-5.0 | 1.0-6.3 | 0.0-0.7 | 0.7-5.3 |
| (average) | (12.6) | (50.2) | (54.0) | (50.8) | (3.9) | (3.7) | (0.2) | (2.5) |
| Commercial pollenizers: | | | | | | | | |
| Sidekick | 14.3 | 46.3 | 33.0 | 24.3 | 2.0 | 4.7 | 0.0 | 0.0 |
| SP-4 | 13.3 | 11.7 | 29.7 | 28.7 | 2.3 | 1.3 | 2.3 | 1.0 |
| Polimax | 14.3 | 10.0 | 18.3 | 18.7 | 1.3 | 1.7 | 1.3 | 1.3 |

2.2.3—Vegetative Types

The hybrids have a relatively compact growth type, with the (average/pollenizer line of the) longest branch falling between 113.5 and 180.0 cm long and the shortest branch being between 57.0 and 80.0 cm long. The average number of primary branches per pollenizer line was between 3 and 3.5. The average number of secondary branches per pollenizer line at 30 cm and at 90 cm was between 56.0 and 88.5 (at 30 cm) and between 77.5 and 144.0 cm. Internode length ranged between 4.3 and 5.3 on average, depending on the line. Leaf length and width is also relatively compact, with leaf widths between 7.1 and 9.4 cm and lengths between 7.8 and 9.1 cm.

Example 3—Use of Pollenizers According to the Invention 3.1—Trial Set-Up

Three trials were carried out in Spain using pollenizers WH9317x, WH9318x, WH9320x and WH9321x for triploid fruit production on the triploid hybrid variety 'Fashion'.
Trial 1:
Location: green house
Trial dimensions: 3600 m$^2$
Transplanting date: 19 Mar. 2010
Harvest date: 16 Jun. 2010
Scheme: pollenizers and triploids were in separate rows, alternating one row of triploid and one row of pollenizer. Distance between rows was 3 meter, distance between plants in a row was 1 meter.
Trial 2:
Location: open field
Trial dimensions: 2500 m$^2$
Transplanting date: 24 Mar. 2010
Harvest date: 6 Jul. 2010
Scheme: pollenizers and triploids were interplanted in the same rows, with pollenizers making up 25% of the total plants. Distance between rows was 3 meters and distance between plants in a row was 1 meter.

Trial 3:
Location: open field
Trial dimensions: 1500 m$^2$
Transplanting date: 20 Mar. 2010
Harvest date: 2 Jul. 2010
Scheme: pollenizers and triploids were interplanted in the same rows, with pollenizers making up 25% of the total plants. Distance between rows was 2 meters and distance between plants in a row was 1.8 meter.
3.2—Trial Results

TABLE 5 mean value* of the triploid fruit weight (kg) of Fashion (triploid hybrid) for three trials carried out in three locations in Spain 2010

| | Trial 1 | Trial 2 | Trial 3 |
|---|---|---|---|
| WH9317x | 5.14 | 4.18 | 4.27 |
| WH9318x | 5.06 | 4.48 | 4.12 |
| WH9320x | 5.22 | 3.94 | 4.23 |
| WH9321x | 4.65 | 4.35 | 4.30 |
| Average | 5.02 | 4.24 | 4.23 |
| (min-MAX) | (2.5-9.08) | (2.5-7.64) | (2.56-7.60) |
| Commercial Pollenizers | | | |
| Jenny | 5.15 | 4.26 | 4.96 |
| Polimax | 5.30 | 3.90 | 4.54 |
| SP-4 | 6.14 | 4.26 | 4.44 |
| Sidekick | 5.35 | | |

*Mean value: mean of the weights of the total marketable triploid fruits (>2.5 kg) harvested in an area of 60 m$^2$, 90 m$^2$ and 30 m$^2$ of the Trial 1, Trial 2 and Trial 3, respectively.

The trial results of Table 5 show that the dual purpose pollenizers of the invention are indeed good pollenizers and lead to good triploid fruit yields.

Example 4

Three further diploid hybrids were developed having dual purpose pollenizer characteristics as described for the above hybrids but having a higher brix content and being thus particularly suitable for fresh consumption similar to apples.

Fruit characteristics—harvested at maturity (method for measurements as in examples 1 and 2)

TABLE 6

| Dual Purpose Pollenizers (diploid hybrids) | Average fruit no. | Average fruit weight (kg) | ° Brix | Fruit flesh structure (kg) | Flesh color (RHS) |
|---|---|---|---|---|---|
| WH9716 | 61.7 | 0.5 | 8.0 | 0.7 | Red (44A) |
| WH9717 | 65.7 | 0.7 | 10.1 | 0.8 | Red (41A) |
| WH9721 | 57.3 | 0.5 | 9.2 | 0.7 | Red (41A) |
| Comparison Polimax | 9.3 | 2.4 | 10.0 | 1.2 | Red (44A) |

TABLE 7

| Pollenizers (diploid hybrids) | Average length (cm) (FRT-cm_L) | Average width (cm) (FRT-cm_D) |
|---|---|---|
| WH9716 | 10.0 | 9.2 |
| WH9717 | 10.4 | 9.7 |
| WH9721 | 11.0 | 9.7 |
| Comparison Polimax | 17.0 | 16.0 |

TABLE 8

| Pollenizers (diploid hybrids) | Average rind thickness - blossom end (cm) (RND-cm_BE;) | Average rind thickness - side (cm) (RND-cm_S) |
|---|---|---|
| WH9716 | 0.2 | 0.2 |
| WH9717 | 0.1 | 0.3 |
| WH9721 | 0.1 | 0.3 |
| Comparison Polimax | 0.5 | 0.5 |

These three dual purpose pollenizers thus produce small diploid edible fruits on the pollinizer plants, which are particularly suitable for being sold for fresh consumption.

Example 5

In another experiment fruit characteristics of the three diploid hybrid pollenizers given in example 4 have been determined.
Trial 4:
Location: Open Field, Acampo Calif. USA N32° 46.530', W115° 33.017', Elevation 16 m, Trial dimensions: 472 m². Transplanting date: 6 Aug. 2012; Harvest date: 17 Oct. 2012. Scheme: The distance between rows (beds) were 5', the distance between plants, 3'.

Fruit characteristics harvested at maturity (Measurement method: see examples 1 and 2). "USDA descriptors" are the plant variety descriptors described for watermelon in the "Objective description of Variety Watermelon (*Citrullus lanatus* (Thunb.) Matsum. & Nakai", ST-470-18 (dated Jul. 1, 2009) as published by U.S. Department of Agriculture, Agricultural Marketing Service, Science and Technology, Plant Variety Protection Office, Beltsville, Md. 20705 (available and which can be downloaded on the world wide web at usda.gov).

TABLE 9

| Characteristics 1)-14) | USDA descriptor | WH 9716 | WH 9717 | WH 9721 | Polimax |
|---|---|---|---|---|---|
| | 1. General Fruit Type | | | | |
| | 1 = Oblong, 2 = Round Large, 3 = Round small (icebox), 4 = round mini | 4 | 4 | 4 | 3 |
| | 2. Area of best adaptation | | | | |
| | 1 = Southern US, 2 = Northeast/Central US, 3 = Southwest US, 4 = Most US Areas 5 = other | 4 | 4 | 4 | 4 |
| | 3. Maturity | | | | |
| | No. of days from emergence to anthesis | — | — | — | — |
| | No. of days from pollination to maturity | 33 | 33 | 33 | 35 |
| | Days Relative Maturity (as reported in seed catalogs) | 75 | 75 | 75 | 78 |
| | Maturity category 1 = early, 2 = medium, 3 = late | 1 | 1 | 1 | 1 |
| | 4. Ploidy | 1 | 1 | 1 | 1 |
| | 1 = diploid, 2 = tetraploid, 3 = triploid 5. PLANT | | | | |
| | Cotyledon shape: 1 = flat, 2 = folded | 1 + 2 | 1 + 2 | 1 + 2 | 1 + 2 |
| | Plant sex form: 1 = monoecious, 2 = andromonoecious | 1 | 1 | 1 | 1 |
| | No. of main stems at crown | 3 | 3 | 3 | 3 |
| 1 | Number of flowers per plant at first fruit set: Staminate | 25.6 | 35.8 | 31.8 | 7.8 |
| | Number of flowers per plant at first fruit set: Pistillate | 1.6 | 2.4 | 3.4 | 3 |
| | Number of flowers per plant at first fruit set: Perfect | 0 | 0 | 0 | 0 |

TABLE 9-continued

| Characteristics 1)-14) | USDA descriptor | WH 9716 | WH 9717 | WH 9721 | Poli-max |
|---|---|---|---|---|---|
| | 6. STEM | | | | |
| | Stem shape (cross section): 1 = round, 2 = angular | 2 | 2 | 2 | 2 |
| 8 | Diameter (mm) at second node | 9.4 | 8.9 | 8.6 | 7.2 |
| | Stem surface: 1 = glabrous, 2 = scabrous, 3 = pubescent, 4 = bristled | 3 | 3 | 3 | 3 |
| 2 | Vine length (cm) (at last harvest) | 109.8 | 128.3 | 110.5 | 155.1 |
| 3 | No. of Internodes (at last harvest) | 19 | 22 | 20.8 | 19 |
| | Ratio Vine length (cm): No of internodes (at last harvest) | 5.8 | 5.8 | 5.3 | 8.2 |
| | 7. LEAF | | | | |
| | Leaf shape: 1 = ovate, 2 = obovate, 3 = round | 1 | 1 | 1 | 1 |
| | Leaf lobes: 1 = none, 2 = lobed | 2 | 2 | 2 | 2 |
| | Leaf length (cm) | 16.4 | 16.0 | 12.7 | 15.5 |
| | Leaf width (cm) | 13.3 | 13.7 | 11.4 | 13.9 |
| | Leaf size: 1 = longer than wide, 2 = length-width equal, 3 = wider than long | 1 | 1 | 1 | 1 |
| | Dorsal surface pubescence: 1 = smooth, 2 = pubescent | 2 | 2 | 2 | 2 |
| | Ventral surface pubescence: 1 = smooth, 2 = pubescent | 2 | 2 | 2 | 2 |
| | Leaf color: 1 = light green, 2 = gray green, 3 = medium green, 4 = dark green | 3 | 3 | 3 | 2 |
| | Color chart name: RHS; Value | 147B | 137B | 137B | 138B |
| | 8. FLOWER | | | | |
| | Diameter across Staminate (cm) | 2.8 | 3.2 | 2.9 | 3.1 |
| | Diameter across Pistillate (cm) | 2.2 | 2.96 | 2.5 | 3.3 |
| | Flower color: 1 = lemon yellow, 2 = yellow, 3 = orange | 2 | 2 | 2 | 2 |
| | Color chart name: RHS; Value | 7B | 7B | 7B | 7A |
| | 9. MATURE FRUIT | | | | |
| | Fruit shape: 1 = round, 2 = oval, 3 = cylindrical | 1 | 2 | 2 | 2 |
| 4 | (cm) Long | 10.7 | 11.4 | 12.0 | 19.6 |
| 5 | Diameter at midsection (cm) | 10.1 | 10.1 | 9.9 | 16.5 |
| 6 | Average weight (kg) | 0.60 | 0.647 | 0.665 | 2.9 |
| 7 | Maximum fruit weight (kg) | 0.81 | 0.83 | 0.848 | 3.7 |
| | Index = length ÷ diameter × 10 | 10.6 | 11.3 | 12.1 | 11.9 |
| | Fruit surface: 1 = smooth, 2 = slightly grooved, 3 = deeply grooved | 1 | 1 | 1 | 1 |
| | Skin color pattern: 1 = solid (one color), 2 = stripe, 3 = mottle/net | 2 | 2 | 2 | 3 |
| | Primary color: 1 = Yellow Green (Desert King), 2 = Light Green (Charleston Gray), 3 = Medium Green (Sugar baby), 4 = dark green (Florida Giant), 5 = Gray Green | 4 | 4 | 4 | 5 |
| | Color chart name: RHS; Value: | N137A | N137A | N137A | 138C |
| | Secondary color 1 = Yellow Green, 2 = Light Green, 3 = Medium green, 4 = dark green | 1 | 1 | 1 | 3 |
| | Color chart name: RHS; Value: | 145D | 145D | 145D | 146A |
| | 10. RIND | | | | |
| | Rind texture: 1 = tender, 2 = brittle, 3 = tough | 2 | 2 | 2 | 2 |
| 9 | Thickness blossom end (mm) | 2.6 | 2.0 | 2.4 | 5.4 |
| 10 | Thickness sides (mm) | 4.4 | 3.4 | 4.1 | 8.6 |
| | 11. FLESH | | | | |
| | Flesh texture: 1 = crisp, 2 = soft | 2 | 2 | 2 | 2 |
| | Flesh coarseness: 1 = course fibrous, 2 = fine - little fiber | 2 | 2 | 2 | 2 |
| 11 | Flesh color: 1 = white, 2 = yellow, 3 = orange, 4 = pink, 5 = red, 6 = dark red | 5 | 5 | 5 | 3 |
| 12 | Refractometer: % Soluble solids of juice (Center of fruit) (Brix) | 8.4 | 8.4 | 9.0 | 10.1 |
| | % Hollow heart | 0 | 0 | 0 | 0 |
| 13 | % placental separation | 0 | 0 | 0 | 6.7 |
| 14 | % traverse crack | 0 | 0 | 0 | 6.7 |
| | 12. SEED | | | | |
| | Seed Size: 1 = Small, 2 = Medium, 3 = Large | 1 | 1 | 1 | 1 |
| | Length (mm) | 5.25 | 5.02 | 4.92 | 5.17 |

TABLE 9-continued

| Characteristics 1)-14) | USDA descriptor | WH 9716 | WH 9717 | WH 9721 | Poli-max |
|---|---|---|---|---|---|
| | Width (mm) | 3.34 | 3.45 | 3.19 | 3.32 |
| | Thickness (mm) | 1.62 | 1.70 | 1.81 | 1.63 |
| | Index = Length ÷ Width × 10 | 15.72 | 14.55 | 15.42 | 15.57 |
| | gm per 1000 Seeds | 10 | 11.5 | 11.8 | 10.8 |
| | No. of seeds per Fruit | 568 | 236 | 372.9 | 2430 |
| | Seed Color: 1 = white, 2 = white-tan tipped, 3 = white-pink tipped, 4 = tan, 5 = green, 6 = red, 7 = dark brown, 8 = dark brown mottled, 9 = black, 10 = mottled black, 11 = other (specify) _____ | 4 + 8 | 8 | 7 | 8 |
| | Color chart name: RHS, Value | 161C + 165A | 165A | 165A | 165A |

Characteristics 1-14 are characteristics in which the diploid pollenizer hybrids of the invention differ (statistically) significantly from the most similar pollenizer Polimax.

These are typical values. Values may vary due to environment. Other values that are substantially equivalent are also within the scope of the invention. For example, Brix is environmentally sensitive which explains the slight differences in brix of ripe fruit between Examples 4 and 5.

All of the patent documents (e.g., patents and published applications) and non-patent literature documents referred to herein are hereby incorporated by reference herein in their entireties.

The invention claimed is:

1. A seed of a watermelon variety designated WH9716, a representative sample of seeds of WH9716 having been deposited under Accession Number NCIMB 42704.

2. A plant, or a part thereof, produced by growing the seed of claim 1.

3. The plant or part thereof of claim 2, produced by in vitro culture or by grafting of a scion derived from WH9716 to a different rootstock, a representative sample of seeds of WH9716 having been deposited under Accession Number NCIMB 42704.

4. A fruit produced on the plant of claim 2.

5. The fruit of claim 4, wherein said fruit has an average rind thickness on the sides of at least 0.2 cm and at most 0.4 cm.

6. A watermelon plant which is regenerated from the plant part of claim 2, wherein the part is a scion, a cutting, a rootstock, a cell, a cotyledon, a fruit, a shoot, a shoot tip, a hypocotyl, an embryo, a seed, a protoplast, a leaf, a meristem, a flower or a stem, a part of any of these, or any combination thereof, and wherein the regenerated plant has all the physiological and morphological characteristics of variety WH9716 when grown under the same conditions, wherein a representative sample of seeds of variety WH9716 has been deposited under accession number NCIMB 42704.

7. A fruit produced on the plant of claim 6.

8. The fruit of claim 7, wherein said fruit has an average rind thickness on the sides of at least 0.2 cm and at most 0.4 cm.

9. The seed of claim 1, wherein the seed is primed and/or wherein the seed further comprises one or more of: a biological control agent, a fungicidal composition, a insecticidal composition, a nematicidal composition, an acaricidal composition, or any combination thereof.

10. The plant of claim 2, wherein the plant comprises a different rootstock.

11. The plant of claim 6, wherein the plant comprises a different rootstock.

12. A method for producing triploid watermelon fruits a field, comprising:
  a) interplanting a triploid watermelon plant and the plant of claim 2 in a field;
  b) allowing pollen from the plant of claim 2 to pollinate flowers of the triploid plant to produce triploid hybrid plants; and
  c) harvesting fruits produced on the triploid hybrid plants.

13. A method for producing triploid watermelon fruits a field, comprising:
  a) interplanting a triploid watermelon plant and the plant of claim 6 in a field;
  b) allowing pollen from the plant of claim 6 to pollinate flowers of the triploid plant to produce triploid hybrid plants; and
  c) harvesting fruits produced on the triploid hybrid plants.

* * * * *